US00PP17030P2

(12) United States Plant Patent
Eskelund Hansen

(10) Patent No.: US PP17,030 P2
(45) Date of Patent: Aug. 22, 2006

(54) ROSE PLANT NAMED 'EVERA 134'

(50) Latin Name: *Rosa hybrida*
Varietal Denomination: Evera 134

(76) Inventor: Rosa Eskelund Hansen, Fiskervænget 9, 5600 Fåborg (DK)

( * ) Notice: Subject to any disclaimer, the term of this patent is extended or adjusted under 35 U.S.C. 154(b) by 0 days.

(21) Appl. No.: 11/021,997

(22) Filed: Dec. 24, 2004

(51) Int. Cl.
*A01H 5/00* (2006.01)

(52) U.S. Cl. ..... Plt./121

(58) Field of Classification Search ..... Plt./101, Plt./121, 128, 148
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of rose plant named 'Evera 134', characterized by its upright, compact and rounded plant habit; dark green-colored leaves; large double light pink-colored flowers; flowers held upright on strong and erect peduncles; and good postproduction longevity.

1 Drawing Sheet

Botanical designation: *Rosa hybrida.*
Cultivar denomination: 'Evera 134'.

BACKGROUND OF THE INVENTION

The present invention relates to a new and distinct cultivar of the Rose class, botanically known as *Rosa hybrida,* commercially known as a potted Rose and hereinafter referred to by the name 'Evera 134'.

The new Rose plant is a product of a planned breeding program conducted by the Inventor in Denmark. The objective of the breeding program was to develop new potted Rose cultivars with novel and attractive flower colors, disease resistance and excellent postproduction longevity.

The new Rose plant originated from a cross-pollination made by the Inventor on Mar. 1, 2002 of two unnamed proprietary *Rosa hybrida* seedlings, not patented. The cultivar Evera 134 was discovered and selected by the Inventor as a flowering plant within the progeny of the stated cross-pollination in a controlled environment in Denmark. Plants of the new cultivar differ primarily from plants of the parent selections primarily in flower color.

Asexual reproduction of the new Rose plant by cuttings in Denmark since Nov. 1, 2003, has shown that the unique features of this new Rose plant are stable and reproduced true to type in successive generations of asexual reproduction.

SUMMARY OF THE INVENTION

The new Rose plant has not been observed under all possible environmental conditions. The phenotype may vary significantly with variations in environment such as temperature and light level, without, however, any variance in genotype.

The following traits have been repeatedly observed and are determined to be the unique characteristics of 'Evera 134'. These characteristics in combination distinguish the new Rose plant as a new and distinct cultivar:

1. Upright, compact and rounded plant habit.
2. Dark green-colored leaves.
3. Large double light pink-colored flowers.

4. Flowers held upright on strong and erect peduncles.
5. Good postproduction longevity.

Plants of the new Rose plant can be compared to plants of the Rose cultivar Pink Ever, not patented. In side-by-side comparisons conducted in Denmark, plants of the new Rose differed from plants of the cultivar Pink Ever in the following characteristics:

1. Plants of the new Rose were more compact than plants of the cultivar Pink Ever.
2. Plants of the new Rose had slightly smaller flowers and fewer petals per flower than plants of the cultivar Pink Ever.
3. Plants of the new Rose and the cultivar Pink Ever differed in flower coloration.

BRIEF DESCRIPTION OF PHOTOGRAPHS

The accompanying colored photographs illustrate typical specimens of the vegetative growth and flowers of the new Rose plant, showing the colors as true as it is reasonably possible to obtain in colored reproductions of this type. Colors in the photographs may differ slightly from the color values cited in the detailed botanical description which more accurately describe the actual colors of the new Rose plant.

The photograph at the top of the sheet comprises a side perspective view of typical plants of the new Rose plant grown in a container in Denmark.

The photographs at bottom of the sheet comprises close-up views of the upper (left) and lower (right) surfaces of typical flowers and leaves of the new Rose plant.

DETAILED BOTANICAL DESCRIPTION

The following observations and measurements describe plants grown in Denmark in 10.5-cm containers in a glass greenhouse and under conditions which closely approximate commercial production conditions during the summer. Plants used for the description were about 15 weeks old. In the following description, color references are made to The Royal Horticultural Society Colour Chart, 1995 Edition, except where general terms of ordinary dictionary significance are used.

Classification:

*Botanical.*—*Rosa hybrida* cultivar Evera 134.

*Commercial.*—Potted Rose.

Parentage:

*Female, or seed, parent.*—Unnamed proprietary seedling, not patented.

*Male, or pollen, parent.*—Unnamed proprietary seedling, not patented.

Propagation:

*Type.*—Terminal or stem cuttings.

*Time to rooting.*—8 to 10 days with soil temperatures of 20° C.

*Root description.*—Fine; freely branching.

Plant description:

*Form.*—Upright, compact and rounded plant habit.

*Plant height.*—About 20 cm.

*Plant width.*—About 17 cm.

*Growth habit.*—Moderately vigorous; suitable for 10.5-cm containers.

*Stem description.*—Branching habit: About two lateral branches per plant. Lateral branch length: About 13 to 19 cm. Lateral branch diameter: About 4 mm. Internode length: About 1 to 1.5 cm. Texture: Smooth, glabrous. Color: 137C. Thorns: Quantity: Sparse. Length: About 4 mm. Diameter: About 4 mm. Shape: Roughly deltoid. Color, immature: 145A. Color, mature: 174D.

*Foliage description.*—Arrangement: Alternately; compound with typically three to five leaflets per leaf, generally symmetrical. Leaf length: About 7 cm to 8 cm. Leaf width: About 5 cm to 6 cm. Leaflet length: About 2 to 4 cm. Leaflet width: About 1 to 2.5 cm. Shape: Ovate. Apex: Acuminate. Base: Obtuse. Margin: Serrulate. Venation pattern: Pinnate. Texture, upper and lower surfaces: Smooth, glabrous; leathery. Petiole length: About 1.5 to 2 cm. Petiole diameter: About 1 mm. Petiole texture, upper and lower surfaces: Smooth, glabrous. Color: Developing and fully expanded foliage, upper surface: Between 139A and 147A. Developing and fully expanded foliage, lower surface: Closest to 191A. Venation, upper surface: 147B. Venation, lower surface: 146C. Petiole, upper and lower surfaces: 146B. Stipules: Shape: Lanceolate; apex, acuminate; base, truncate; margin, serrate. Length: About 5 mm. Width: About 1 mm. Texture, upper and lower surfaces: Leathery, smooth. Color, upper surface: Closest to 137B. Color, lower surface: Closest to 137C to 137D.

Flower description:

*Flower type and habit.*—Large double light pink-colored flowers. Consistently symmetrical rosette flowers that are hemispherical in shape. Flowers borne singly on erect and strong peduncles; about two to three flowers and flower buds per plant. Flowers persistent.

*Flowering season.*—Year-round under greenhouse conditions, optimal flowering from spring through autumn under garden conditions; flowering intermittent.

*Flower diameter.*—About 5 to 6 cm.

*Flower depth* (*height*).—About 2.5 to 3 cm.

*Flower longevity on plant.*—About two weeks.

*Fragrance.*—None detected.

*Flower buds* (*at stage of showing color*).—Shape: Ovoid. Length: About 2 cm. Diameter: About 1.5 cm. Color: 146B.

*Petals.*—Quantity: About 23 per flower. Length: About 2 to 3 cm. Width: About 1 to 3.5 cm. Shape: Broadly obovate. Apex: Rounded. Base: Attenuate. Margin: Entire. Texture, upper and lower surfaces: Smooth, glabrous; satiny. Color: When opening, upper and lower surfaces: 36D. Fully opened, upper surface: 36D. Fully opened, lower surface: 36D; towards the margins, 150D.

*Sepals.*—Quantity per flower: Typically five. Calyx length: About 3 cm. Calyx diameter: About 8 mm. Shape: Linear; falcate. Apex: Sharply pointed. Base: Truncate. Texture, upper and lower surfaces: Pubescent. Color, upper and lower surfaces: Close to 137A.

*Peduncles.*—Strength: Strong, but flexible. Aspect: Mostly erect. Length: About 4 cm. Diameter: About 3 mm. Texture: Smooth, glabrous. Color: 144A.

*Reproductive organs.*—Stamens: Quantity: About 100 per flower. Anther length: About 2 mm. Anther shape: Oval. Anther color: 17C. Pollen color: Closest to 23B to 23C. Pistils: Quantity: About 65 per flower. Pistil length: About 7 mm. Stigma color: 145B. Style color: 140B. Receptacle shape: Cup-like. Receptacle size: About 8.5 mm by 6 mm. Receptacle texture: Smooth, glabrous. Receptacle color: Closest to 144A.

*Seed/fruit.*—Seed and fruit production has not been observed.

Disease/pest resistance: Plants of the new Rose have not been shown to be resistant to pathogens and pests common to Rose plants.

Temperature tolerance: Plants of the new rose have been shown to be tolerant to temperatures from 0 to 45° C.

It is claimed:

1. A new and distinct rose plant named 'Evera 134', as illustrated and described.

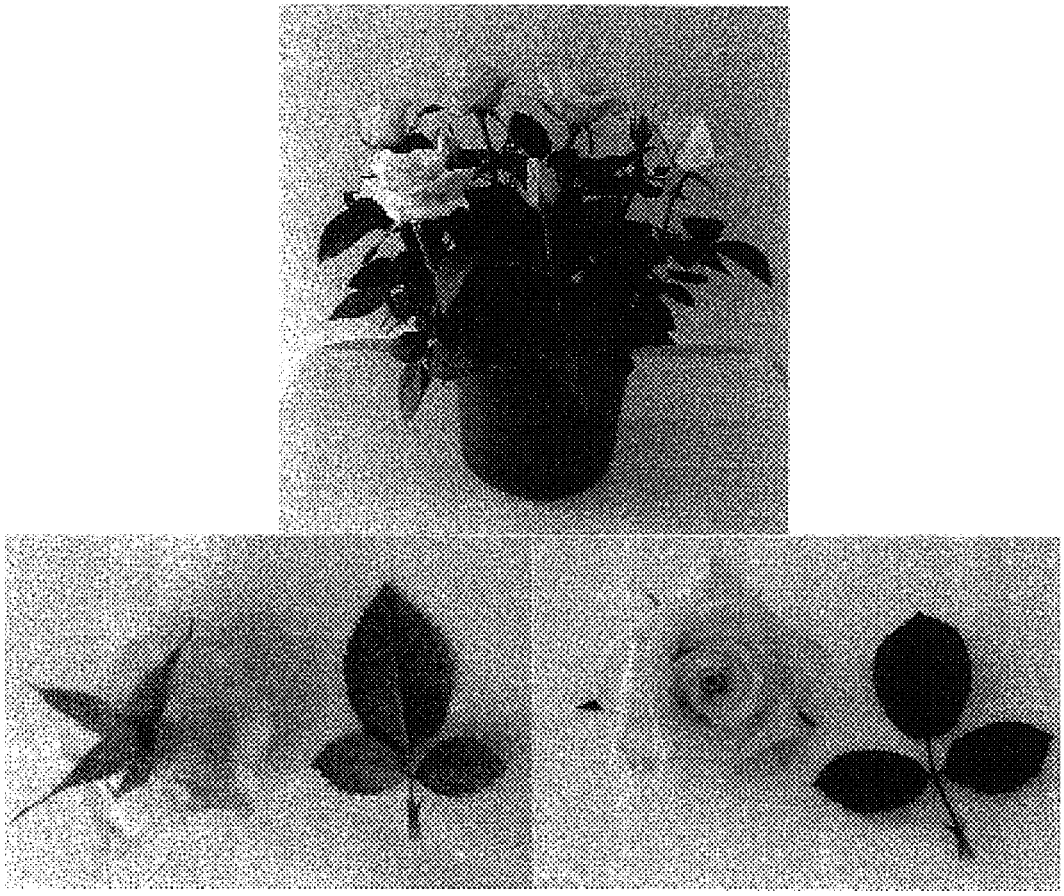

* * * * *